(12) United States Patent
Limbach

(10) Patent No.: US 12,383,449 B2
(45) Date of Patent: Aug. 12, 2025

(54) BLACK LIGHT IN REMOTE DEVICE FOR PATIENT SUPPORT APPARATUS

(71) Applicant: Baxter Medical Systems GmbH + Co. KG, Saalfeld (DE)

(72) Inventor: Tobias Limbach, Munich (DE)

(73) Assignee: Baxter Medical Systems GmbH + Co. KG, Saalfeld (DE)

( * ) Notice: Subject to any disclaimer, the term of this patent is extended or adjusted under 35 U.S.C. 154(b) by 1334 days.

(21) Appl. No.: 17/036,580

(22) Filed: Sep. 29, 2020

(65) Prior Publication Data

US 2021/0093497 A1    Apr. 1, 2021

Related U.S. Application Data

(60) Provisional application No. 62/908,847, filed on Oct. 1, 2019.

(51) Int. Cl.
| | |
|---|---|
| *A61G 7/05* | (2006.01) |
| *A47C 21/00* | (2006.01) |
| *A61L 2/08* | (2006.01) |
| *A61L 2/10* | (2006.01) |

(52) U.S. Cl.
CPC .............. *A61G 7/05* (2013.01); *A47C 21/003* (2013.01); *A61L 2/084* (2013.01); *A61L 2/10* (2013.01); *A47C 21/00* (2013.01); *A61G 2203/12* (2013.01); *A61G 2203/16* (2013.01); *A61G 2203/20* (2013.01); *A61L 2202/16* (2013.01); *A61L 2202/20* (2013.01)

(58) Field of Classification Search
CPC .... A61G 7/05; A61G 7/0524; A61G 2203/16; A61G 2203/20; A61L 2/084; A61L 2/10; A61L 2202/16; A61L 2202/20; A47C 21/003; A47C 21/00
USPC ............................................ 5/600, 905, 658
See application file for complete search history.

(56) References Cited

U.S. PATENT DOCUMENTS

| | | | | |
|---|---|---|---|---|
| 1,574,226 | A * | 2/1926 | Ackermann | A47D 9/02 |
| | | | | 5/101 |
| 5,375,276 | A * | 12/1994 | Nelson | A61G 1/06 |
| | | | | 5/503.1 |
| 6,234,642 | B1 * | 5/2001 | Bokamper | F21V 33/0072 |
| | | | | 362/130 |
| 7,250,615 | B1 * | 7/2007 | Soong | A61L 2/10 |
| | | | | 250/493.1 |

(Continued)

FOREIGN PATENT DOCUMENTS

| | | | | |
|---|---|---|---|---|
| AU | 2006268288 A1 * | 2/2008 | ........... | A61B 5/6891 |
| AU | 2006268288 B2 * | 12/2011 | ........... | A61B 5/6891 |

(Continued)

*Primary Examiner* — Robert G Santos
(74) *Attorney, Agent, or Firm* — Price Heneveld LLP

(57) ABSTRACT

A handheld contamination detection device for a healthcare setting includes a body having a top surface, a bottom surface, and an end surface extending between the top surface and the bottom surface. A light source is coupled to the end surface. The light source emits ultraviolet light away from the body. A user-interface is coupled to the top surface of the body. The user-interface includes a touch screen. A controller is communicatively coupled with the light source and the user-interface. The controller receives a command input from the user-interface and activates the light source in response to the command input.

18 Claims, 6 Drawing Sheets

(56) References Cited

U.S. PATENT DOCUMENTS

| | | | |
|---|---|---|---|
| 8,105,532 B2 * | 1/2012 | Harmon | A61L 2/10 250/493.1 |
| 8,226,887 B2 * | 7/2012 | Harmon | A61L 2/10 250/493.1 |
| 9,095,633 B1 * | 8/2015 | Dayton | A61L 2/10 |
| 9,588,057 B2 | 3/2017 | Clark | |
| 9,615,983 B2 * | 4/2017 | Stryker | A01N 59/20 |
| 9,669,121 B2 | 6/2017 | Liao et al. | |
| 10,004,654 B2 | 6/2018 | Zerhusen et al. | |
| 10,086,097 B2 * | 10/2018 | Dayton | A61L 2/24 |
| 10,183,085 B2 | 1/2019 | Dobrinsky et al. | |
| 10,293,066 B2 * | 5/2019 | Dayton | G08C 17/02 |
| 11,224,670 B2 * | 1/2022 | Dayton | A61L 2/24 |
| 11,395,776 B2 * | 7/2022 | Xu | A61G 1/013 |
| 11,723,817 B2 * | 8/2023 | Xu | A61G 1/04 5/611 |
| 11,857,688 B2 * | 1/2024 | Dayton | A61L 2/10 |
| 2004/0034933 A1 * | 2/2004 | Smith | H05B 47/19 5/602 |
| 2006/0223731 A1 | 10/2006 | Carling | |
| 2010/0104471 A1 * | 4/2010 | Harmon | A61L 2/10 422/186.3 |
| 2012/0093688 A1 * | 4/2012 | Harmon | A61L 2/10 250/455.11 |
| 2012/0119110 A1 | 5/2012 | Hirsch et al. | |
| 2012/0196375 A1 | 8/2012 | Granja et al. | |
| 2013/0117936 A1 * | 5/2013 | Stryker | A61L 2/235 422/24 |
| 2016/0093412 A1 | 3/2016 | Liao et al. | |
| 2016/0121007 A1 * | 5/2016 | Dayton | A61L 2/10 250/492.1 |
| 2017/0112953 A1 * | 4/2017 | Dayton | G08C 17/02 |
| 2017/0320083 A1 | 11/2017 | Hayward | |
| 2019/0022261 A1 * | 1/2019 | Dayton | A61L 2/24 |
| 2021/0093497 A1 * | 4/2021 | Limbach | G01N 21/29 |
| 2021/0113394 A1 * | 4/2021 | Xu | A61G 1/013 |
| 2022/0088246 A1 * | 3/2022 | Dayton | A61L 2/24 |
| 2022/0313507 A1 * | 10/2022 | Xu | A61G 1/0275 |
| 2023/0190132 A1 * | 6/2023 | Trepanier | A61B 5/746 600/532 |
| 2025/0073360 A1 * | 3/2025 | Payne | A61L 2/24 |

FOREIGN PATENT DOCUMENTS

| | | | | |
|---|---|---|---|---|
| CN | 205626552 U | 10/2016 | | |
| EP | 3799779 A1 * | 4/2021 | | A61B 5/0059 |
| EP | 3799779 B1 * | 12/2023 | | A61B 5/0059 |
| JP | S63298140 A | 12/1988 | | |
| WO | 2013070906 A1 | 5/2013 | | |
| WO | 2018140072 A1 | 8/2018 | | |
| WO | WO-2025049496 A1 * | 3/2025 | | A61L 2/08 |

* cited by examiner

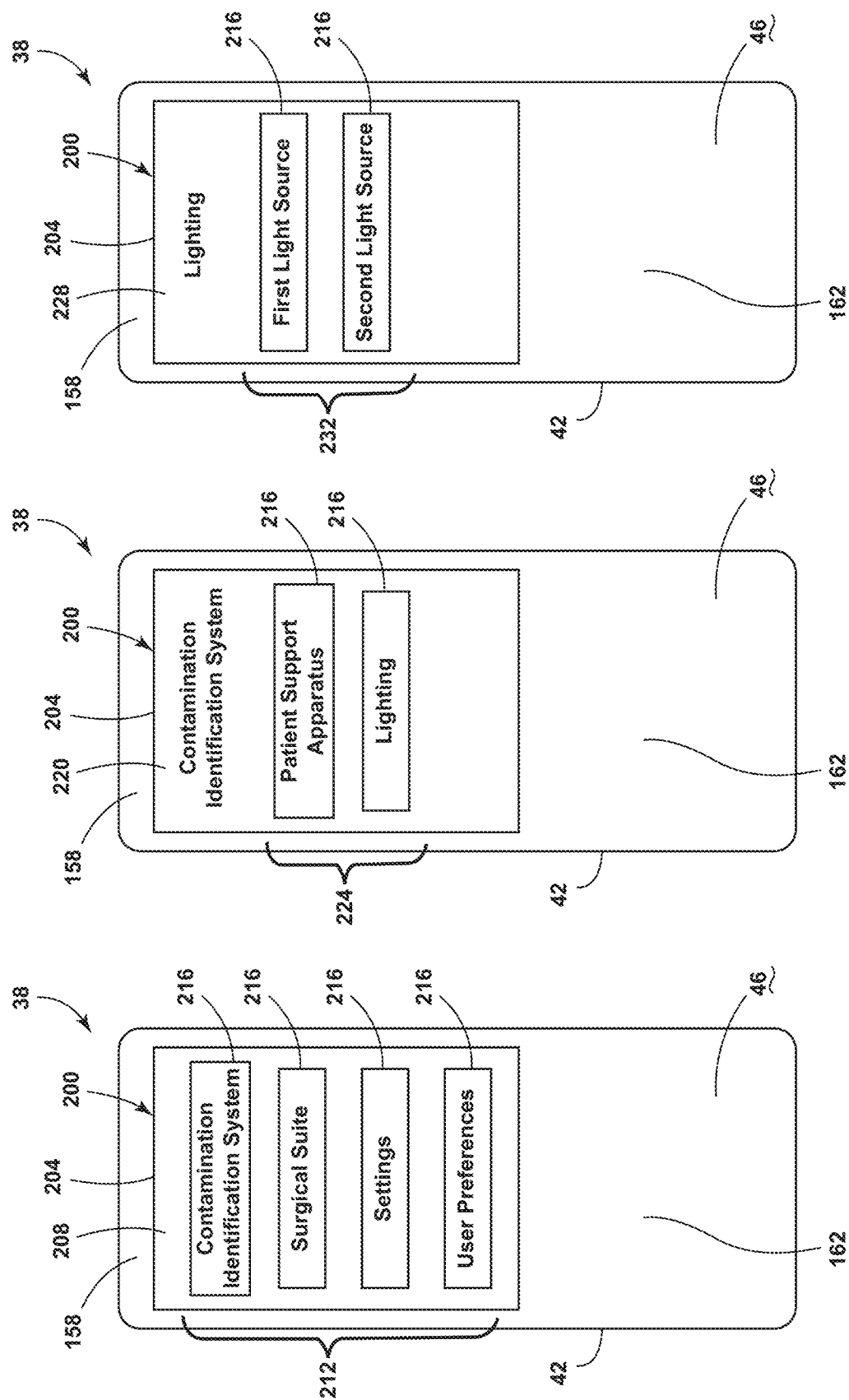

BLACK LIGHT IN REMOTE DEVICE FOR PATIENT SUPPORT APPARATUS

CROSS-REFERENCE TO RELATED APPLICATION

This application claims priority to and the benefit under 35 U.S.C. § 119(e) of U.S. Provisional Application No. 62/908,847, filed on Oct. 1, 2019, entitled "BLACK LIGHT IN REMOTE DEVICE FOR PATIENT SUPPORT APPARATUS," the disclosure of which is hereby incorporated herein by reference in its entirety.

FIELD OF THE DISCLOSURE

The present disclosure generally relates to a remote device configured to emit black light to illuminate contamination on a patient support apparatus.

SUMMARY OF THE DISCLOSURE

According to one aspect of the present disclosure, a contamination identification system includes a patient support apparatus that includes a support frame disposed on a base. A first light source is coupled to the patient support apparatus. The first light source emits visible light toward a support surface of the support frame. A first controller is operably coupled to the patient support apparatus. The first controller activates the first light source to emit the visible light. A contamination detection device includes a body and a second light source coupled to the body and that emits ultraviolet light. A second controller is disposed in the body that activates the second light source to illuminate contamination on the patient support apparatus. A user-interface for receiving a command input relating to at least one of the first light source and the second light source is coupled to the body and communicatively coupled to the second controller.

According to another aspect of the present disclosure, a contamination identification system for a healthcare setting includes a contamination detection device including: a body, a first light source coupled to the body, and a controller operably coupled to the first light source. The controller activates the first light source to emit ultraviolet light to illuminate contamination within said healthcare setting. A second light source is communicatively coupled with the controller. The controller activates the second light source to emit visible light to illuminate said healthcare setting. Healthcare equipment is disposed within said healthcare setting. The contamination detection device is freely movable relative to the healthcare equipment to illuminate the contamination on the healthcare equipment.

According to yet another aspect of the present disclosure, a handheld contamination detection device for a healthcare setting includes a body having a top surface, a bottom surface, and an end surface extending between the top surface and the bottom surface. A light source is coupled to the end surface. The light source emits ultraviolet light away from the body. A user-interface is coupled to the top surface of the body. The user-interface includes a touch screen. A controller is communicatively coupled with the light source and the user-interface. The controller receives a command input from the user-interface and activates the light source in response to the command input.

These and other features, advantages, and objects of the present disclosure will be further understood and appreciated by those skilled in the art by reference to the following specification, claims, and appended drawings.

BRIEF DESCRIPTION OF THE DRAWINGS

In the drawings:

FIG. 6A is a top plan view of a remote contamination detection device with a user-interface that has a first display screen, according to the present disclosure;

FIG. 6B is a top plan view of a remote contamination detection device with a user-interface that has a second display screen, according to the present disclosure;

FIG. 6C is a top plan view of a remote contamination detection device with a user-interface that has a third display screen, according to the present disclosure.

DETAILED DESCRIPTION

Figure 1:
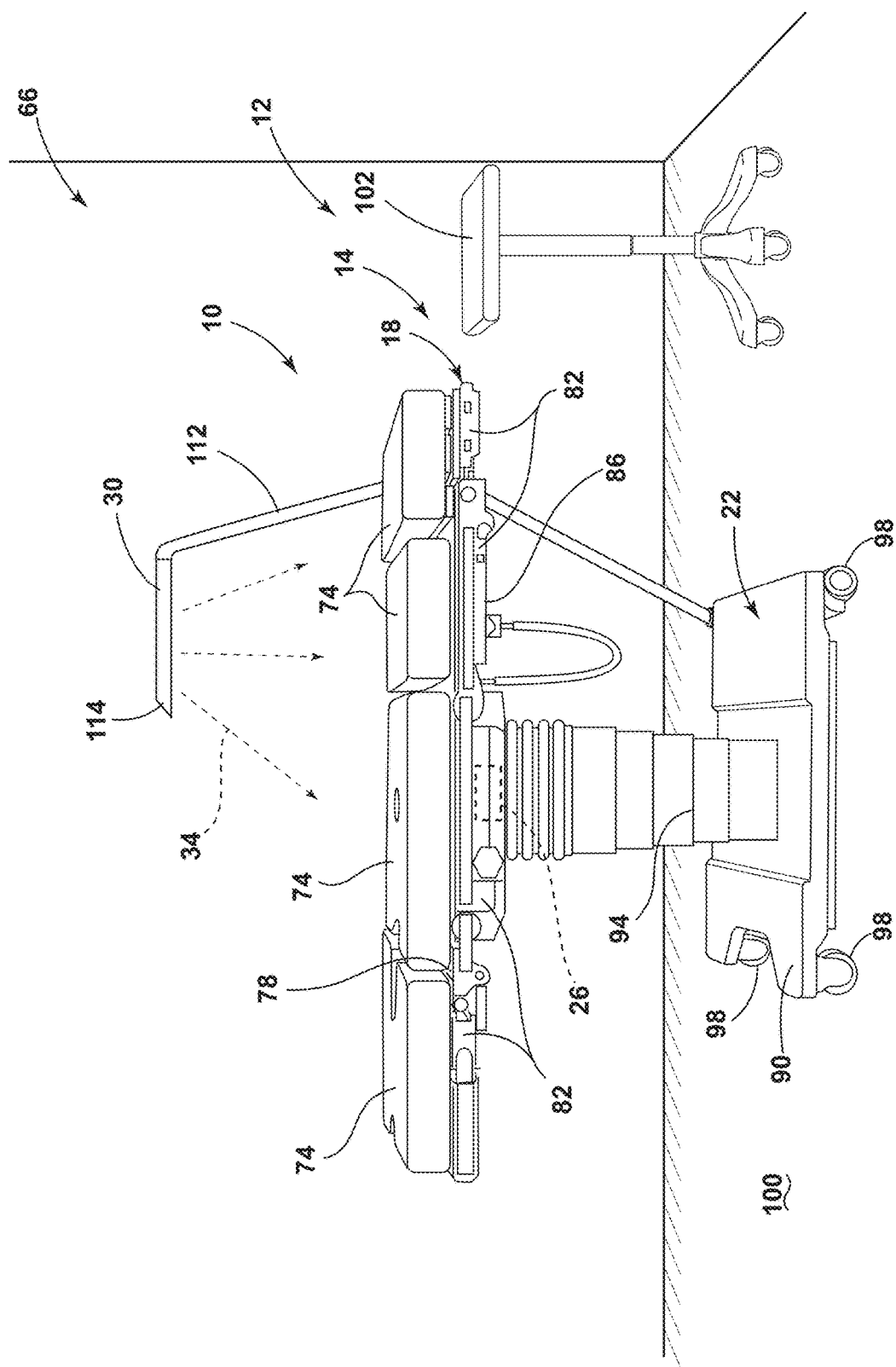
FIG. 1 is a top side perspective view of a patient support apparatus, according to the present disclosure.

The present illustrated embodiments reside primarily in combinations of method steps and apparatus components related to a black light in a remote device for a patient support apparatus. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to a surface closest to an intended viewer, and the term "rear" shall refer to a surface furthest from the intended viewer. However, it is to be understood that the disclosure may assume various alternative orientations, except where expressly specified to the contrary. It is also to be understood that the specific structures and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-7, reference numeral 10 generally designates a contamination identification system that includes healthcare equipment 12, such as a patient support apparatus 14 that has a support frame 18 and a base 22. A first controller 26 is operably coupled to the patient support apparatus 14. A first light source 30 is operably coupled to the patient support apparatus 14. The first light source 30 emits visible light 34 toward the patient support apparatus 14. A contamination detection device 38 includes a body 42 that has a top surface 46 and an end surface 50. The contamination detection device 38 includes a second controller 54 and a second light source 58 that emits ultraviolet light 62 when activated by the second controller 54 to illuminate contamination on the patient support apparatus 14.

Referring to FIG. 1, the patient support apparatus 14 is illustrated as a surgical table within a healthcare setting 66, such as a surgical suite. The patient support apparatus 14 includes the support frame 18 for supporting the patient thereon. One or more pads 74 may be selectively disposed on a top support surface 78 of the support frame 18. As illustrated in FIG. 1, multiple pads 74 are arranged along the top support surface 78 of the support frame 18. The pads 74 may be disposed in a spaced-apart arrangement along the top support surface 78, or alternatively, may be directly coupled to one another. Alternatively, the support frame 18 may include a single pad 74 covering at least a portion of the top support surface 78.

The support frame 18 generally includes a plurality of segments 82 that are each pivotally coupled to one or two adjacent segments 82. The segments 82 are independently movable relative to one another. In this way, a single segment 82 may be rotated to an incline, rotated to a decline, or otherwise moved relative to the remaining stationary segments 82. The independently movable segments 82 may be advantageous for aligning the patient on the support frame 18 for one or more surgical procedures or other treatment of the patient.

According to various aspects, the patient support apparatus 14 includes the base 22 coupled to a bottom surface 86 of the support frame 18. The base 22 includes a support feature 90 and a central pedestal 94 extending between the support feature 90 and the support frame 18. While the patient support apparatus 14 is illustrated with a single central pedestal 94, it is contemplated that other configurations of the base 22 are contemplated without departing from the teachings herein (e.g., more than one pedestal 94 may extend between the support feature 90 and the support frame 18, etc.). The support feature 90 includes rollers 98 that engage an underlying floor surface 100. In this way, the patient support apparatus 14 is transportable about the surgical suite or otherwise within a hospital, medical facility, or other healthcare setting 66.

The patient support apparatus 14 configured as the surgical table is generally used during one or more surgical procedures. During a surgical procedure, biological material or fluids may be deposited on the patient support apparatus 14, on other healthcare equipment 12 (e.g., such as an instrument table 102, etc.), or otherwise deposited in the surgical suite. The fluids may include medicinal fluid, bodily fluid (e.g., mucus, blood, saliva, urine, etc.), or a combination thereof. Such material may be considered contamination deposited on the patient support apparatus 14 or elsewhere in the surgical suite. The contamination may be deposited as a result of one or more procedures or may be foreign contaminants shed by the patient or personnel in the surgical suite. As a result of the contamination, the surgical suite, the patient support apparatus 14, and the other healthcare equipment 12 are cleaned following the surgical procedure. The floor surface 100 of the surgical suite may be relatively easy to clean, whereas the patient support apparatus 14 may be more difficult to clean due to different surface configurations of the support frame 18, the base 22, the roller 98, etc. The different surfaces and/or shape of the components of the support frame 18 and the base 22 may increase the difficulty of visibility or accessibility of the contamination on the patient support apparatus 14.

Figure 2:
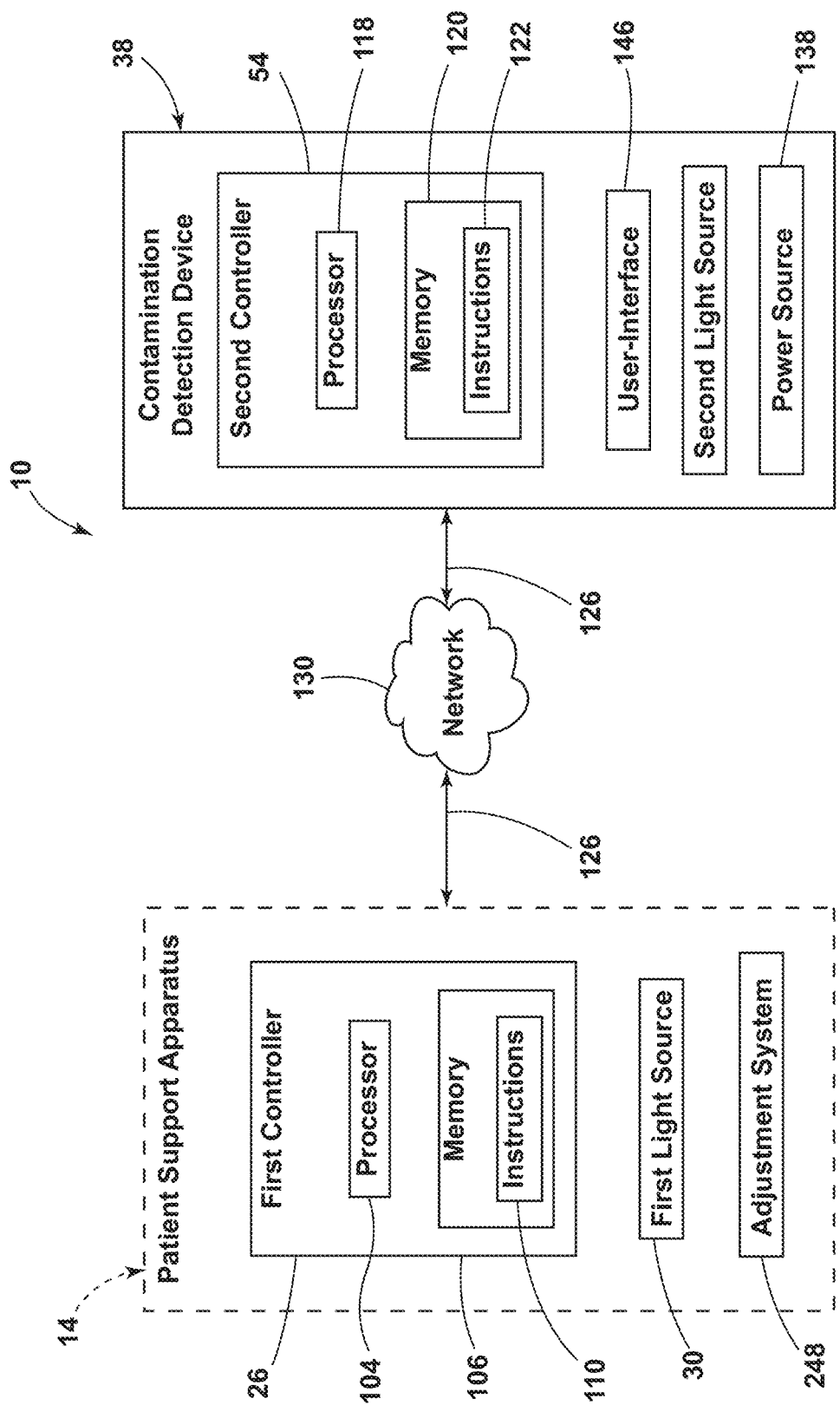
FIG. 2 is a diagram of a communication interface between a first controller of a patient support apparatus and a second controller of a remote contamination detection device, according to the present disclosure.

Referring still to FIG. 1, as well as FIG. 2, the patient support apparatus 14 includes the first controller 26. The first controller 26 includes a processor 104, a memory 106, and other control circuitry. The first controller 26 includes routines or instructions 110 stored within the memory 106 and executable by the processor 104. In various examples, the first controller 26 includes light control circuitry for controlling the first light source 30. In this way, the first controller 26 is configured to control the function of the first light source 30, such as, for example, activation, deactivation, direction, intensity, etc.

In the illustrated configuration, the first light source 30 is coupled to the base 22 of the patient support apparatus 14. It is contemplated that the first light source 30 may be directly coupled to various locations of the patient support apparatus 14 without departing from the teachings herein, such as, for example, the base 22, the support frame 18, siderails, etc. In other examples, the first light source 30 is communicatively coupled with the first controller 26, but may not have a direct mechanical connection to the patient support apparatus 14. For example, the first light source 30 may be an overhead lighting assembly disposed within the surgical suite.

Referring still to FIGS. 1 and 2, the first light source 30 emits the visible light 34 toward the top support surface 78 of the patient support apparatus 14. The first light source 30 may be movable or static relative to the patient support apparatus 14. As illustrated, the first light source 30 includes an arm 112 and a light source housing 114. The arm 112 is adjustable to adjust the light source housing 114 between various positions relative to the patient support apparatus 14 to provide different lighting effects during the surgical procedure, to illuminate the surgical suite, or a combination thereof. It may be advantageous for the first light source 30 to be movable relative to the patient support apparatus 14 to provide the visible light 34 at various locations on the support frame 18. Further, it may be advantageous for the first light source 30 to be movable to reduce or prevent shadowing effects on the support frame 18 or the patient during surgical procedures that can be caused by the angled direction of the visible light 34.

In various examples, the visible light 34 is generally visible to the human eye and has a wavelength in a range from about 380 nm to 740 nm. The first light source 30 may include any form of light source. For example, fluorescent lighting, light-emitting diodes (LEDs), organic LEDs (OLEDs), polymer LEDs (PLEDs), laser diodes, quantum dot LEDs (OD-LEDs), solid-state lighting, a hybrid, or any other similar device. Any other form of lighting may be utilized within the patient support apparatus 14 or the first light source 30 without departing from the teachings herein. Further, various types of LEDs are suitable for use as the first light source 30, including, but not limited to, top-emitting LEDs, side-emitting LEDs, and others. Moreover, according to various examples, multicolored light sources such as Red, Green, and Blue (RGB) LEDs that employ red, green, blue LED packaging may be used to generate various desired colors of light outputs from a single light source, according to known light color mixing techniques.

The first light source 30 may be configured as a single light. In a non-limiting example, the first light source 30 may be a single LED. Alternatively, the first light source 30 may be configured as multiple lights that may be disposed in various locations relative to the patient support apparatus 14. In examples where the first light source 30 is configured as multiple lights, the first controller 26 may selectively control each light of the first light source 30, such that one, all, or a portion of the lights can be activated at any given time. Additionally or alternatively, the patient support apparatus 14 can include one or more circuits or circuit boards coupled to the first light source 30. The circuit boards may be printed circuit boards, which may be configured as flexible or rigid printed circuit boards.

Referring still to FIGS. 1 and 2, each of the first and second controllers 26, 54 are configured for gathering input, processing the input, and generating an output response to the input. The first and second controllers 26, 54 are communicatively coupled to one another. A communication interface 126 may be established between the contamination detection device 38 and the patient support apparatus 14 for bidirectional communication between the first and second controllers 26, 54. For example, the second controller 54 of the contamination detection device 38 may receive a command input. If the command input is related to the first light source 30, the second controller 54 sends a signal to the first controller 26 regarding the command input for the first light source 30. The first controller 26 then sends a corresponding signal to operate the first light source 30 in accordance with the command input.

The first and second controllers 26, 54 communicate by a network 130. The network 130 may be one or more various wired or wireless communication mechanisms, including any combination of wired (e.g., cable and fiber) and/or wireless communications and any network topology or topologies. Exemplary communication networks 130 include wireless communication networks, such as, for example, a Bluetooth® transceiver, a ZigBee® transceiver, a Wi-Fi transceiver, an IrDA transceiver, an RFID transceiver, etc. It is also contemplated that each of the first and second controllers 26, 58 may include separate transmitters and receivers without departing from the teachings herein. The first and second controllers 26, 54 generally include circuitry configured for bidirectional wireless communication. Additional exemplary communication networks 130 include local area networks (LAN) and/or wide area networks (WAN), including the Internet and other data communication services. It is contemplated that the first and second controllers 26, 54 may communicate by any suitable technology for exchanging data.

In examples where the first and second controllers 26, 54 communicate via a Bluetooth® transceiver, the contamination detection device 38 and the patient support apparatus 14 may be linked or synchronized (e.g., synced). The contamination detection device 38 may be associated with multiple patient support apparatuses 14 by linking each individual patient support apparatus 14 to the contamination detection device 38 via Bluetooth®. In such examples, the contamination detection device 38 may be linked to a single patient support apparatus 14 at any given time, or alternatively, may be synced to multiple patient support apparatuses 14 at any given time.

Figure 3:
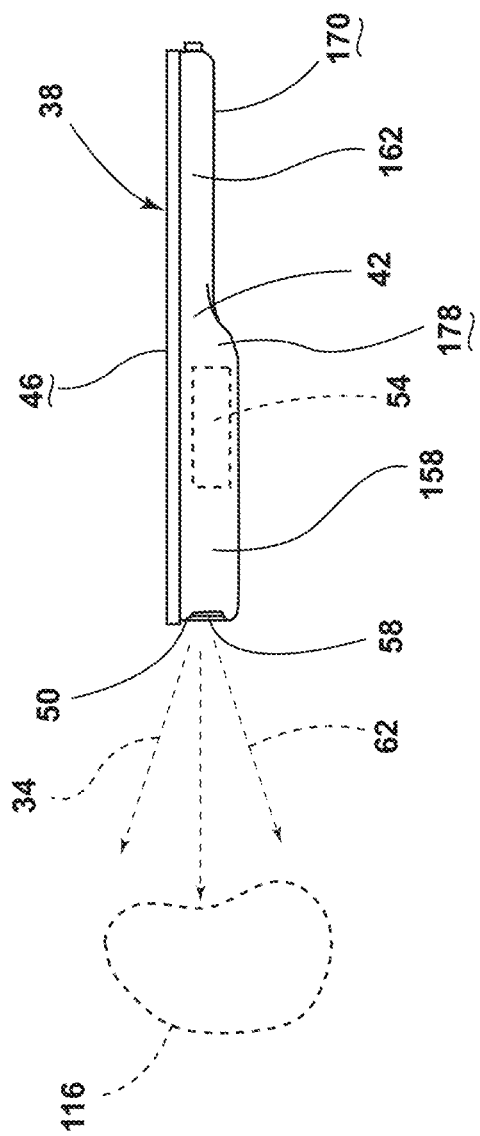
FIG. 3 is a side plan view of a remote contamination detection device of a contamination identification system, according to the present disclosure.

Referring still to FIG. 2, as well as FIG. 3, as previously stated, the contamination identification system 10 includes the contamination detection device 38. The contamination detection device 38 includes the second light source 58, which emits the ultraviolet light 62 when activated by the second controller 54. The ultraviolet light 62 emitted by the second light source 58 may have a wavelength in a range from about 10 nm to about 400 nm. Accordingly, the ultraviolet light 62 may include UV-A light, UV-B light, UV-C light, or a combination thereof. In certain aspects, the ultraviolet light 62 may have a wavelength in a range of from about 320 nm to about 400 nm, such that the second light source 58 emits black light (e.g., UV-A light).

The ultraviolet light 62 is generally not visible to a human eye, however, a portion of the ultraviolet light 62 may be visible. Typically, the human eye can respond to wavelengths in a range of from about 380 nm to about 740 nm (e.g., within the visible light spectrum). Accordingly, it may be difficult to determine where the ultraviolet light 62 is directed. In order to determine if the entire surface of the patient support apparatus 14 or other healthcare equipment 12 has been checked for contamination, the medical personnel may utilize a direction confirmation 116 provided by the contamination detection device 38. The direction confirmation 116 may be a visible indication on the surface of the patient support apparatus 14 or the other healthcare equipment 12. For example, at least a portion of the ultraviolet light 62 emitted by the second light source 58 may be generally visible to a human eye. The ultraviolet light 62 that overlaps with the visible light spectrum (e.g., wavelengths in a range from about 380 nm to about 400 nm) may be at least partially visible to the human eye and may operate as the direction confirmation 116.

Additionally or alternatively, the contamination detection device 38 may also emit the visible light 34 simultaneously with the ultraviolet light 62 to provide the direction confirmation 116. The visible light 34 may not substantially interfere with the illumination of the contamination provided by the ultraviolet light 62. In certain aspects, the visible light 34 emitted by the second light source 58 may have a wavelength close to the wavelength of the ultraviolet light 62. For example, the visible light 34 may include a violet light (having a wavelength in a range from about 380 nm to about 450 nm) or a blue light (having a wavelength in a range from about 380 nm to about 500 nm). The violet or blue light may allow the user of the contamination detection device 38 to see where the ultraviolet light 62 is being directed without substantially interfering with the illumination of the contamination. It is contemplated that the visible light 34 emitted by the second light source 58 may have any wavelength within the visible spectrum without departing from the teachings herein.

Similar to the first light source 30, the second light source 58 may include any form of light source. For example, fluorescent lighting, light-emitting diodes (LEDs), organic LEDs (OLEDs), polymer LEDs (PLEDs), laser diodes, quantum dot LEDs (OD-LEDs), solid-state lighting, a hybrid, or any other similar device. Any other form of lighting may be utilized within the patient support apparatus 14 without departing from the teachings herein. Further, various types of LEDs are suitable for use as the second light source 58, including, but not limited to, top-emitting LEDs, side-emitting LEDs, and others. Moreover, according to various examples, multicolored light sources such as Red, Green, and Blue (RGB) LEDs that employ red, green, blue LED packaging may be used to generate various desired colors of light outputs from a single light source, according to known light color mixing techniques.

Referring still to FIGS. 2 and 3, the second light source 58 may be configured as a single light, such as a single LED. Alternatively, the second light source 58 may be configured as multiple lights. In examples where the second light source 58 is configured as multiple lights, the second controller 54 may selectively control each light of the second light source 58 such that one, all, or a portion of the lights can be activated at any given time. Additionally or alternatively, the contamination detection device 38 can include one or more circuits or circuit boards coupled to the second light source 58. In circuit board examples, the circuit boards may be printed circuit boards, which may be configured as flexible or rigid printed circuit boards.

According to various aspects, the contamination detection device 38 includes the second controller 54 communicatively coupled to the second light source 58 to control the second light source 58. The second controller 54 may include a processor 118, a memory 120, and other control circuitry. The second controller 54 includes routines or instructions 122 stored within the memory 120 and executable by the processor 118. The second controller 54 may execute software to automatically control the second light source 58.

The contamination detection device 38 includes a power source 138, such as a battery. The battery is generally stored within the body 42. It is contemplated that the power source 138 may be replaceable batteries or may be rechargeable batteries. In rechargeable battery examples, the contamination detection device 38 may define a port for receiving a charger to charge the rechargeable battery. Additionally or alternatively, the power source 138 may be outside of the body 42. For example, the contamination detection device 38 may include a power receiving port to receive a cord, which can connect the contamination detection device 38 to the power source 138.

Referring still to FIGS. 2 and 3, the contamination detection device 38 includes the body 42 having the top surface 46 and the end surface 50. The second light source 58 is generally coupled to the end surface 50. In various aspects, the second light source 58 is configured to direct the ultraviolet light 62 outwardly from the contamination detection device 38 and away from a user. The ultraviolet light 62 may be configured as a directed light beam, which may reduce or prevent the emission of scattered ultraviolet light 62. For example, the second light source 58 may be configured as a laser to direct the ultraviolet light 62. It is also contemplated that the contamination detection device 38 may include optics configured to direct or collimate the ultraviolet light 62. The contamination detection device 38 may be configured such that the user may grasp the contamination detection device 38 and direct the ultraviolet light 62 away from the user. Accordingly, the end surface 50 where the second light source 58 is coupled is a distal end 158 of the contamination detection device 38 relative to the user.

The body 42 of the contamination detection device 38 is generally configured to form a more ergonomic grasp for the user. In this way, the distal end 158 of the contamination detection device 38 has a greater thickness than a proximal end 162. The thicker distal end 158 may be advantageous for housing the second controller 54, the second light source 58, the associated circuitry, the power source 138, or a combination thereof. The proximal end 162 having a lesser thickness may be advantageous to improve the grasp of the user on the contamination detection device 38.

To form the ergonomic shape of the contamination detection device 38, the top surface 46 is a substantially continuous, planar surface. A bottom surface 170 of the contamination detection device 38 has a first surface at the distal end 158 and a second surface at the proximal end 162, which is offset from the first surface by a sloped surface. The bottom surface 170 may include a slope, a step, or other transition portion between the distal and proximal ends 158, 162. The bottom surface 170 may be generally planar, or alternatively, may be curved. In certain aspects, at least the bottom surface 170 adjacent to the proximal end 162 may be curved to provide a more ergonomic grasping location for the user. Additionally or alternatively, corners between the top surface 46 and side surfaces 178 as well as corners between the bottom surface 170 and the side surfaces 178 may be rounded to contribute to the ergonomic grasping location.

Figure 5:
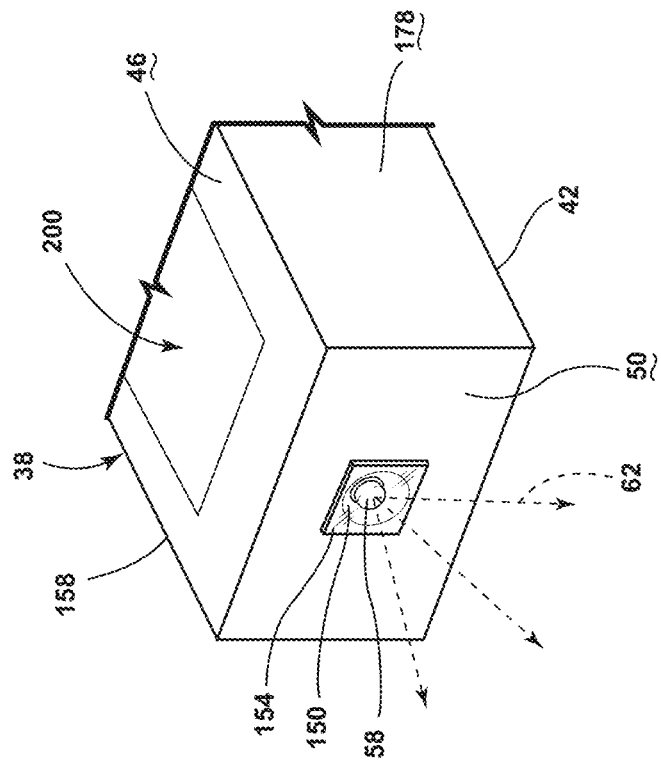
FIG. 5 is a partial front perspective view of a contamination detection device, according to the present disclosure.
Figure 4:
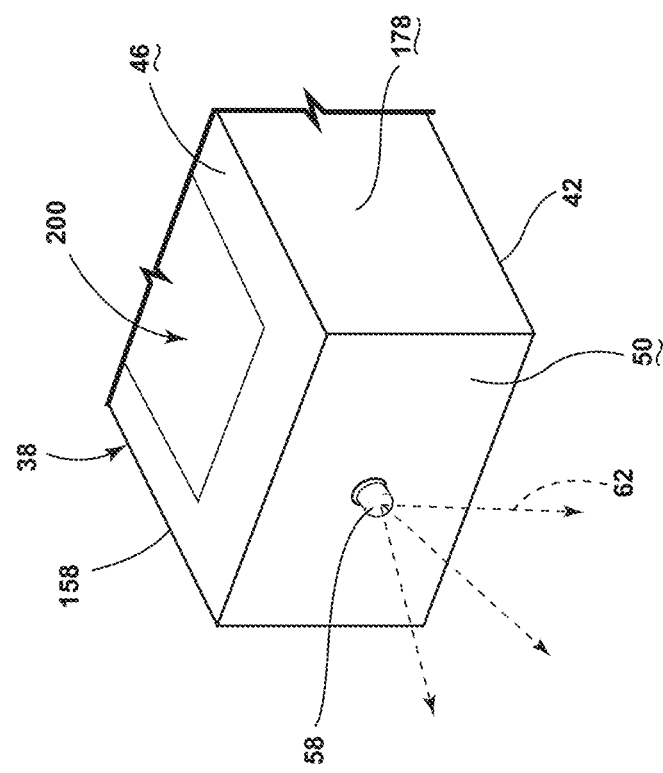
FIG. 4 is a partial front perspective view of a contamination detection device, according to the present disclosure.

Referring to FIGS. 4 and 5, the second light source 58 may be coupled to the body 42 in different configurations. For example, as illustrated in FIG. 4, the end surface 50 of the body 42 is planar and the second light source 58 extends outward from the end surface 50. Accordingly, the second light source 58 may be a projection extending from the body 42. Alternatively, as illustrated in FIG. 5, the end surface 50 of the body 42 of the contamination detection device 38 may extend at least partially around the second light source 58. Accordingly, the end surface 50 defines a channel or recessed portion 150, and the second light source 58 is disposed within the recessed portion 150. In such examples, the surface of the recessed portion 150 surrounding the second light source 58 may be configured as a light guide to direct the ultraviolet light 62 in the selected direction outwardly from the contamination detection device 38. A window or lens 154 may extend over the recessed portion 150 to enclose the second light source 58. The lens 154 generally does not substantially interfere with the emission of the ultraviolet light 62 of the visible light 34. The lens 154 may be advantageous for preventing the contamination from entering a space defined by the recessed portion 150. The lens 154 may also be advantageous for providing more convenient cleaning of the contamination detection device 38. It is contemplated that the lens 154 may include the optics for directing the ultraviolet light 62. It is also contemplated that a protective cover may be disposed around the contamination detection device 38 to provide more convenient cleaning and minimize or prevent contamination on the contamination detection device 38.

Referring to FIGS. 6A-6C, the contamination detection device 38 includes a user-interface 200. The user-interface 200 is generally coupled to or integrally formed with the top surface 46 of the contamination detection device 38. The user-interface 200 is disposed on the distal end 158 of the contamination detection device 38, thereby allowing the user to grasp the proximal end 162 of the contamination detection device 38 without interfering with the user-interface 200. Further, the user may grasp the contamination detection device 38 and the user-interface 200 may remain visible and accessible to the user.

In various examples, the user-interface 200 may include a touch-sensitive display screen or a touch screen 204. The touch screen 204 may utilize any practicable touch screen technology (e.g., resistive, capacitive, etc.). The user-interface 200 displays or presents a first display screen 208 having first user options 212. As illustrated in FIG. 6A, the first user options 212 include selectable features 216 that relate to the contamination identification system 10, the surgical suite, settings, and user preferences. The first display screen 208 is generally a home screen or a default screen for the contamination detection device 38. The first display screen 208 may be customizable by the user and may be personalized for each user.

The user selects one of the selectable features 216, which results in the first display screen 208 changing to a second display screen 220. The second display screen 220 illustrated in FIG. 6B appears when the user selects the selectable feature 216 relating to the contamination identification system 10. The second display screen 220 includes second user options 224 corresponding or associated with the selectable feature 216 the user selected from the first display screen 208. Accordingly, the second display screen 220 is a second level screen relative to the first display screen 208 (e.g., displayed after one user input). As illustrated in FIG. 6B, the selectable features 216 on the second display screen 220 correspond to functions or settings of the patient support apparatus 14 and lighting.

The user selects one of the selectable features 216 on the second display screen 220, which results in the second display screen 220 changing to a third display screen 228. The third display screen 228 includes third user options 232. As illustrated in FIG. 6C, the third user options 232 correspond with the lighting functions selected from the second display screen 220. Accordingly, the selectable features 216 on the third display screen 228 correspond with the operation of first and second light sources 30, 58. The third display screen 228 operates as a third level display screen relative to the first display screen 208 (e.g., displayed after two user inputs). It is contemplated that the selectable features 216 relating to the first and second light sources 30, 58 may change the third display screen 228 into another subsequent display screen.

The levels of display screens may be advantageous for preventing inadvertent activation of a function of the contamination detection device 38 or the patient support apparatus 14. In this way, the second user options 224 are displayed in response to a selection of one of the first user options 212, and the third user options 232 are displayed in response to selection of one of the second user options 224. Additionally or alternatively, the user-interface 200 may include a selectable lock feature that prevents the touch screen 204 from receiving and responding to a user input. This may be advantageous for preventing inadvertent selection of the selectable features 216 and may also operate as a power saving mode for the contamination detection device 38.

Referring still to FIGS. 6A-6C, the touch screen 204 may include a variety of selectable features 216 configured as buttons, graphical icons, etc. Additional exemplary selectable features 216 may include a help feature, a battery status indicator, a network indicator, a sync indicator, etc. When a selection is made by the user, a subsequent display screen is displayed on the user-interface 200. In this way, selecting the desired selectable feature 216 (e.g., button or icon) may provide access to the corresponding subsequent display screen in order to control various functions of the contamination identification system 10 or other features of the surgical suite. It is contemplated that additional or fewer selectable features 216 may be included in the user-interface 200 without departing from the teachings herein.

According to various aspects, the user-interface 200 may return to a selected display screen (e.g., a home screen) after a predetermined amount of time has elapsed since user interaction with the user-interface 200. Additionally or alternatively, the touch screen 204 may be an illuminated screen.

In such examples, the touch screen 204 may illuminate in response to user interaction with the user-interface 200. The illumination may be deactivated or dimmed after a predetermined amount of time has elapsed since the user interaction with the user-interface 200. While the user-interface 200 is illustrated as the touch screen 204, it is contemplated that any suitable form of user input, such as soft key, buttons, switches, similar tactile features, touch features, or combinations thereof may be included on the contamination detection device 38. Additionally or alternatively, the contamination detection device 38 may include a display that is not touch-sensitive, but the display may change between the first, second, and third display screens 208, 220, 228 in response to the user interacting with other features that receive the user input (e.g., soft keys, switches, etc.). The selectable features 216 illustrated in FIGS. 6A-6C are merely exemplary and are not meant to be limiting.

Figure 7:
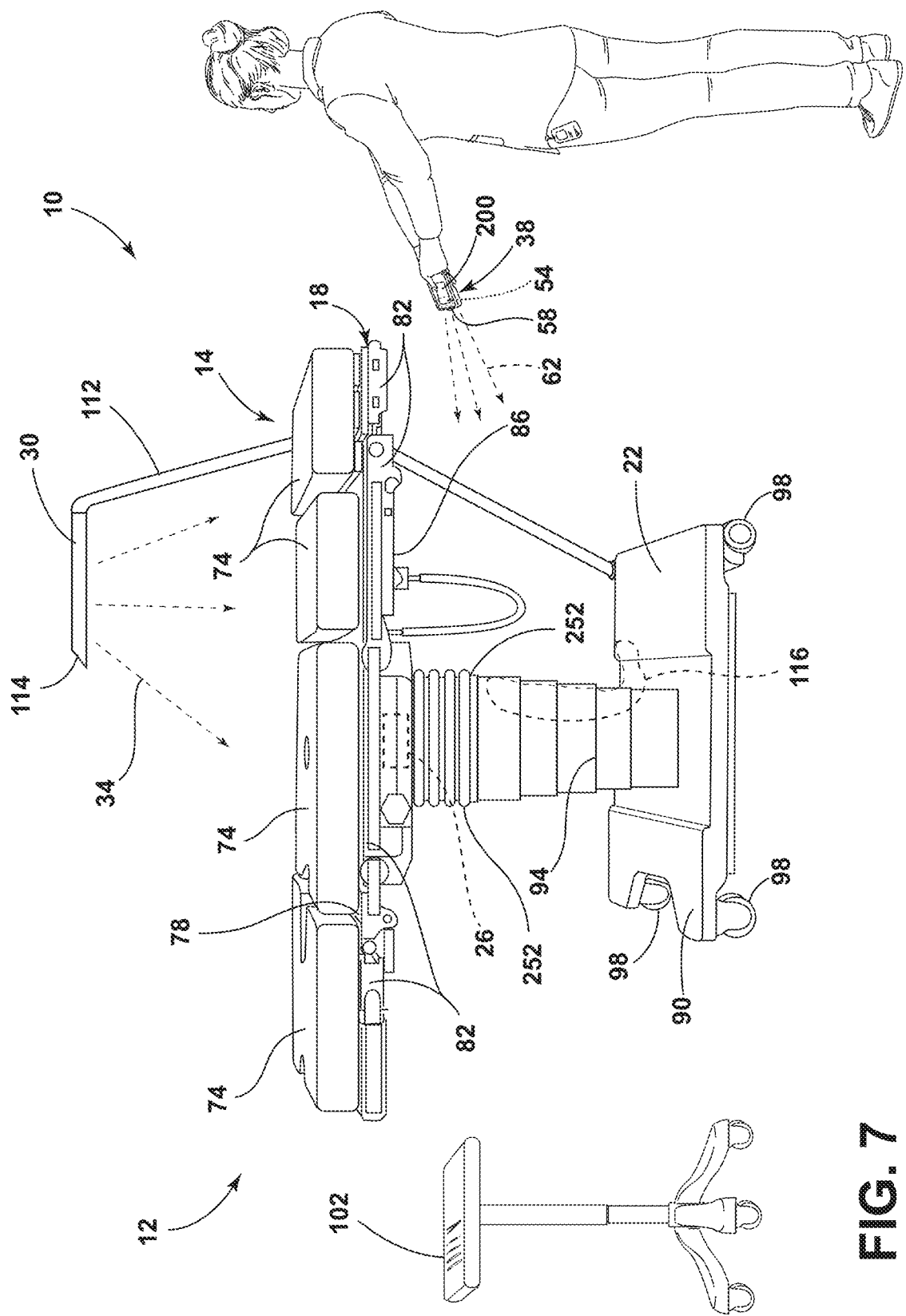
FIG. 7 is a top side perspective view of a contamination identification system in a surgical suite during use, according to the present disclosure.

Referring to FIG. 7, as well as to FIGS. 1-6C, the second controller 54 operates to control the functions of the contamination detection device 38. The second controller 54 is communicatively coupled to the user-interface 200 and controls the user-interface 200 to selectively display a specific display screen. The selectable feature 216 selected by the user is communicated to the second controller 54 as the command input.

After receiving the information or command input from the user-interface 200, the second controller 54 sends a corresponding signal in order to control the operation or function of the respective feature that corresponds with the selectable feature 216 chosen by the user. For example, if the user wants to activate the second light source 58, the user can navigate through the respective levels of the user-interface 200 (e.g., the first, second, and third display screens 208, 220, 228) to select the selectable feature 216 relating to the second light source 58. The user-interface 200 communicates the command input to the second controller 54, which then controls the second light source 58 accordingly. The operation may relate to activation, deactivation, intensity, color, combinations thereof, etc.

In another non-limiting example, if the user wants to activate the first light source 30, the user can navigate through the levels of the user-interface 200 to select the selectable feature 216 corresponding to the first light source 30. The user-interface 200 communicates the command input selection to the second controller 54, which then communicates the command input to the first controller 26 of the patient support apparatus 14. Once the first controller 26 receives the command input from the second controller 54, the first controller 26 operates the first light source 30 based on the command input. The operation may relate to activation, deactivation, intensity, color, combinations thereof, etc.

The contamination detection device 38 is generally a handheld remote device, which is freely movable relative to the healthcare equipment 12. The user may hold the contamination detection device 38 and move the contamination detection device 38 to direct the ultraviolet light 62 along the surface of the healthcare equipment 12 within the healthcare setting 66.

The healthcare setting 66 may be the illustrated surgical suite, however, the contamination detection device 38 may be utilized in other healthcare settings 66. For example, the contamination detection device 38 may be used in hospitals, urgent care centers, doctor offices, rehabilitation centers, nursing homes, long-term care facilities, outpatient services or centers, in-home healthcare settings, etc. The contamination detection device 38 may be utilized in any healthcare setting 66 by the medical professional, the patient, or a combination thereof to optimize cleaning processes of any of the healthcare equipment 12. Additionally or alternatively, the healthcare equipment 12 includes the patient support apparatus 14, the instrument table 102, instruments on the instrument table 102, utility columns, surgical and exam lights, the first light source 30, storage features, imaging devices, the pads 74 on the patient support apparatus 14, etc. The contamination may be a result of the surgical procedures or shed by the patient or by the personnel. The contamination may also be transferred between healthcare equipment 12 by the medical personnel during treatment or surgical procedures. Accordingly, the contamination detection device 38 may be used to detect contamination on any of the healthcare equipment 12. The contamination detection device 38 may not be directly coupled (e.g., free of a mechanical connection) to the patient support apparatus 14 or any other healthcare equipment 12, which is advantageous for increasing the mobility of the contamination detection device 38.

For the illustrated patient support apparatus 14, during surgical procedures or operations, the contamination may be deposited on the patient support apparatus 14. The contamination is at least partially deposited on the support frame 18 or the base 22, including the support frame 18 and the central pedestal 94. For example, the support frame 18 includes the movable segments 82. Contamination may be deposited on or between the segments 82. The base 22 generally includes an adjustment system 248 within a protective shroud 252. The adjustment system 248 adjusts the support frame 18 relative to the base 22 (e.g., height, angles, etc.). Accordingly, the protective shroud 252 is flexible and may have grooves or folds based on the position of the support frame 18. Contamination may be deposited within the grooves and folds of the protective shroud 252.

The contamination may also be deposited on the floor surface 100 and on or within the rollers 98. If the patient support apparatus 14 is moved, the rollers 98 may be adjusted on or over fluids on the floor surface 100. The contamination in various locations on the patient support apparatus 14 may be difficult for the user to see when cleaning the patient support apparatus 14 after the procedure as a result of the different surfaces or shapes of the various features on the patient support apparatus 14. The ultraviolet light 62 from the contamination detection device 38 can illuminate contamination (e.g., fluids) on the patient support apparatus 14, allowing the user to see the contamination remaining on the patient support apparatus 14 that should be cleaned further.

Generally, the patient support apparatus 14 is cleaned and reprocessed after each use. Cleaning is time consuming and, depending on the grade or amount of contamination, can take up to about thirty minutes to clean a single patient support apparatus 14. The entire patient support apparatus 14 and related accessories (e.g., the pads 74) are cleaned before the patient support apparatus 14 is used for another patient. The contamination detection device 38 illuminates blood or other fluids (e.g., the contamination), even in places that may be more difficult to reach for cleaning. It may be advantageous to deactivate the first light source 30 to more easily see the illuminated contamination. However, it is contemplated that the contamination detection device 38 may illuminate the contamination with the ultraviolet light 64 with the first light source 30 illuminating the healthcare setting 66. The contamination detection device 38 may be utilized to confirm that the patient support apparatus 14, the floor surface 100, and other healthcare equipment 12 are sufficiently cleaned. The contamination detection device 38 may increase efficiency of the cleaning processes, as well as provide a confirmation of the level of cleanliness of the equipment or environment.

Use of the present device may provide a variety of advantages. For example, the contamination detection device 38 may be movable relative to the patient support apparatus 14, such that the ultraviolet light 62 may be directed to a variety of locations on the patient support apparatus 14. Additionally, the cleaning process for the patient support apparatus 14 or the surgical suite can be time-consuming, and the ultraviolet light 62 may increase the efficiency of the cleaning process by illuminating the contamination remaining on the patient support apparatus 14. Further, the ultraviolet light 62 illuminates the contamination in hard-to-reach spaces on the patient support apparatus 14. The hard-to-reach spaces may be more difficult to clean, such that contamination may remain after an initial cleaning of the patient support apparatus 14. In this way, the ultraviolet light 62 of the contamination detection device 38 may illuminate the remaining contamination for cleaning. Moreover, the cleaning process generally includes cleaning the pads 74 and the support frame 18, as well as, the support feature 90, the central pedestal 94, and the rollers 98 of the base 22. The contamination detection device 38 may be moved by the user to illuminate contamination that may remain on each of the components of the patient support apparatus 14, and thereby increase efficiency and effectiveness of the cleaning process. Also, the contamination detection device 38 may be utilized to detect contamination on a variety of healthcare equipment 12 in various healthcare settings 66. Further, the contamination detection device 38 may be utilized to control the first light source 30 operably coupled with the patient support apparatus 14. Additional benefits or advantages of using this device may also be realized and/or achieved.

A contamination identification system includes a patient support apparatus that includes a support frame disposed on a base. A first light source is coupled to the patient support apparatus. The first light source emits visible light toward a support surface of the support frame. A first controller is operably coupled to the patient support apparatus. The first controller activates the first light source to emit the visible light. A contamination detection device includes a body and a second light source coupled to the body and that emits ultraviolet light. A second controller is disposed in the body that activates the second light source to illuminate contamination on the patient support apparatus. A user-interface for receiving a command input relating to at least one of the first light source and the second light source is coupled to the body and communicatively coupled to the second controller.

According to another aspect, the contamination detection device is a remote device free of a direct mechanical connection to the patient support apparatus.

According to another aspect, the contamination detection device communicates with the patient support apparatus via a wireless communication interface.

According to another aspect, the first light source is activated through the command input received by the user-interface when the first controller is communicatively coupled with the second controller.

According to another aspect, the user-interface includes a touch screen coupled to a top surface of the body.

According to another aspect, the touch screen displays a first display screen with first user options and a second display screen with second user options. The second display screen is displayed after a selection of one of the first user options.

According to another aspect, the visible light has a wavelength in a range of 380 nm to 740 nm and the ultraviolet light has a wavelength in a range from 320 nm to 400 nm.

According to another aspect of the present disclosure, a contamination identification system for a healthcare setting includes a contamination detection device including: a body, a first light source coupled to the body, and a controller operably coupled to the first light source. The controller activates the first light source to emit ultraviolet light to illuminate contamination within said healthcare setting. A second light source is communicatively coupled with the controller. The controller activates the second light source to emit visible light to illuminate said healthcare setting. Healthcare equipment is disposed within said healthcare setting. The contamination detection device is freely movable relative to the healthcare equipment to illuminate the contamination on the healthcare equipment.

According to another aspect, the healthcare equipment includes a patient support apparatus.

According to another aspect, the second light source is coupled to the patient support apparatus.

According to another aspect, the patient support apparatus includes a controller communicatively coupled to the controller of the contamination detection device for activating the second light source.

According to another aspect, the contamination detection device includes a user-interface coupled to the body for receiving a command input relating to at least one of the first light source and the second light source.

According to another aspect, the user-interface displays a first display screen with first user options and a second display screen with second user options. The first user options and the second user options are different.

According to another aspect, the second user options relate to controlling the first light source.

According to another aspect of the present disclosure, a handheld contamination detection device for a healthcare setting includes a body having a top surface, a bottom surface, and an end surface extending between the top surface and the bottom surface. A light source is coupled to the end surface. The light source emits ultraviolet light away from the body. A user-interface is coupled to the top surface of the body. The user-interface includes a touch screen. A controller is communicatively coupled with the light source and the user-interface. The controller receives a command input from the user-interface and activates the light source in response to the command input.

According to another aspect, the light source emits visible light simultaneously with the ultraviolet light as a direction confirmation.

According to another aspect, the user-interface includes a first display screen having first user options and a second display screen having second user options. The second user options are displayed in response to a selection of one of the first user options.

According to another aspect, the second user options include selectable features for activating or deactivating the light source.

According to another aspect, a first end of the body has a greater thickness than a second end to provide a grasping location.

According to another aspect, the ultraviolet light has a wavelength in a range from 320 nm to 400 nm.

It will be understood by one having ordinary skill in the art that construction of the described disclosure and other components is not limited to any specific material. Other exemplary embodiments of the disclosure disclosed herein may be formed from a wide variety of materials unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, are illustrative only. Although only a few embodiments of the present innovations have been described in detail in this disclosure, those skilled in the art who review this disclosure will readily appreciate that many modifications are possible (e.g., variations in sizes, dimensions, structures, shapes, and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

What is claimed is:

1. A contamination identification system, comprising:
a patient support apparatus including a support frame disposed on a base;
a first light source directly coupled to the patient support apparatus, wherein the first light source emits visible light toward a support surface of the support frame;
a first controller operably coupled to the patient support apparatus, wherein the first controller activates the first light source to emit the visible light; and
a contamination detection device freely movable relative to the patient support apparatus, the contamination detection device including:
a body;

a second light source coupled to the body and that emits ultraviolet light;

a second controller disposed in the body and that activates the second light source to illuminate contamination on the patient support apparatus, wherein the second controller is communicatively coupled to the first controller for activating the second light source; and a user-interface for receiving a command input relating to at least one of the first light source and the second light source, wherein the user-interface is coupled to the body and communicatively coupled to the second controller, and wherein the user-interface includes a touch screen coupled to a top surface of the body.

2. The contamination identification system of claim 1, wherein the contamination detection device is a remote device free of a direct mechanical connection to the patient support apparatus.

3. The contamination identification system of claim 2, wherein the contamination detection device communicates with the patient support apparatus via a wireless communication interface.

4. The contamination identification system of claim 1, wherein the first light source is activated through the command input received by the user-interface.

5. The contamination identification system of claim 1, wherein the touch screen displays a first display screen with first user options and a second display screen with second user options, wherein the second display screen is displayed after a selection of one of the first user options.

6. The contamination identification system of claim 1, wherein the visible light has a wavelength in a range of 380 nm to 740 nm and the ultraviolet light has a wavelength in a range from 320 nm to 400 nm.

7. The contamination identification system of claim 1, wherein the second light source emits the visible light simultaneously with the ultraviolet light as a direction confirmation.

8. The contamination identification system of claim 1, wherein the first light source is directly coupled to the base of the patient support apparatus.

9. A contamination identification system for a healthcare setting, comprising:
a contamination detection device including:
a body;
a first light source coupled to the body; and
a controller operably coupled to the first light source, wherein the controller activates the first light source to emit ultraviolet light to illuminate contamination within said healthcare setting;
a second light source communicatively coupled with the controller, wherein the controller activates the second light source to emit visible light to illuminate said healthcare setting; and
healthcare equipment including a patient support apparatus disposed within said healthcare setting, wherein the second light source is directly coupled to a base of the patient support apparatus, and wherein the contamination detection device is freely movable relative to the healthcare equipment to illuminate the contamination on the healthcare equipment, and wherein the patient support apparatus includes a controller communicatively coupled to the controller of the contamination detection device for activating the second light source.

10. The contamination identification system of claim 9, wherein the contamination detection device includes a user-interface coupled to the body for receiving a command input relating to at least one of the first light source and the second light source.

11. The contamination identification system of claim 10, wherein the user-interface displays a first display screen with first user options and a second display screen with second user options, wherein the first user options and the second user options are different.

12. The contamination identification system of claim 11, wherein the second user options relate to controlling the first light source.

13. A handheld contamination detection device for a healthcare setting, comprising:
a body having a top surface, a bottom surface, and an end surface extending between the top surface and the bottom surface;
a light source coupled to the end surface, wherein the light source emits ultraviolet light away from the body;
a user-interface coupled to the top surface of the body, wherein the user-interface includes a touch screen; and
a controller communicatively coupled with the light source, the user-interface, and at least one piece of healthcare equipment in said healthcare setting, wherein the controller receives a command input from the user-interface and activates the light source in response to the command input, and wherein the controller receives an additional command input from the user-interface and activates a light attached to the at least one piece of healthcare equipment in response to the additional command input.

14. The handheld contamination detection device of claim 13, wherein the light source emits visible light simultaneously with the ultraviolet light as a direction confirmation.

15. The handheld contamination detection device of claim 13, wherein the user-interface includes a first display screen having first user options and a second display screen having second user options, and wherein the second user options are displayed in response to a selection of one of the first user options.

16. The handheld contamination detection device of claim 15, wherein the second user options include selectable features for activating or deactivating the light source.

17. The handheld contamination detection device of claim 13, wherein a first end of the body has a greater thickness than a second end to provide a grasping location.

18. The handheld contamination detection device of claim 13, wherein the ultraviolet light has a wavelength in a range from 320 nm to 400 nm.

* * * * *